United States Patent
Wang et al.

(10) Patent No.: US 10,792,247 B2
(45) Date of Patent: Oct. 6, 2020

(54) ORAL TRANSMUCOSAL COMPOSITIONS INCLUDING AROMATASE INHIBITORS FOR LOW TESTOSTERONE LEVELS IN MEN

(71) Applicant: Professional Compounding Centers of America, Houston, TX (US)

(72) Inventors: Tsu-I Catherine Wang, Sugar Land, TX (US); Bruce Vincent Biundo, Houston, TX (US)

(73) Assignee: Professional Compounding Centers of America, Houston, TX (US)

( * ) Notice: Subject to any disclaimer, the term of this patent is extended or adjusted under 35 U.S.C. 154(b) by 0 days.

(21) Appl. No.: 16/291,706

(22) Filed: Mar. 4, 2019

(65) Prior Publication Data
US 2019/0192421 A1 Jun. 27, 2019

Related U.S. Application Data

(63) Continuation of application No. 15/328,443, filed as application No. PCT/US2015/041560 on Jul. 22, 2015, now abandoned, which is a continuation of application No. 14/337,783, filed on Jul. 22, 2014, now abandoned.

(51) Int. Cl.
| | |
|---|---|
| *A61K 9/00* | (2006.01) |
| *A61K 9/68* | (2006.01) |
| *A61K 47/42* | (2017.01) |
| *A61K 47/38* | (2006.01) |
| *A61K 47/36* | (2006.01) |
| *A61K 47/10* | (2017.01) |
| *A61K 9/20* | (2006.01) |
| *A61K 31/4196* | (2006.01) |
| *A61K 9/06* | (2006.01) |

(52) U.S. Cl.
CPC ............ *A61K 9/006* (2013.01); *A61K 9/0056* (2013.01); *A61K 9/0058* (2013.01); *A61K 9/06* (2013.01); *A61K 9/2018* (2013.01); *A61K 31/4196* (2013.01); *A61K 47/10* (2013.01); *A61K 47/36* (2013.01); *A61K 47/38* (2013.01); *A61K 47/42* (2013.01)

(58) Field of Classification Search
None
See application file for complete search history.

(56) References Cited

U.S. PATENT DOCUMENTS

2002/0150596 A1* 10/2002 Carter .................... A61K 47/10
424/400
2008/0026040 A1* 1/2008 Farr ....................... A61K 31/18
424/443

OTHER PUBLICATIONS

Google Patent Search—buccal patch gelatin pectin xanthan aromatase inhibitor_May 31, 2020 (Year: 2020).*

* cited by examiner

*Primary Examiner* — Michael P Cohen
(74) *Attorney, Agent, or Firm* — David G. Woodral; GableGotwals

(57) ABSTRACT

Formulations for oral transmucosal compositions that include aromatase inhibitors (AIs) in combination with transmucosal absorption enhancers are disclosed. Disclosed oral transmucosal compositions may be for immediate release or slow release, and may be administered to increase bloodstream testosterone levels and thereby reduce symptoms of testosterone deficiency. Disclosed oral transmucosal compositions may include liquid dosage forms, solid dosage forms, and chewing gums. Further dosage forms may include mucoadhesive thin strips, thin films, tablets, patches, and tapes, among others. Other dosage forms may be: mucoadhesive liquids such as gel-forming liquid; gel-forming; semisolids; and gel-forming powders, among other dosage forms that exhibit mucoadhesive properties, and provide oral transmucosal delivery of AIs. Disclosed oral transmucosal compositions may allow the delivery of AIs directly into the patient's bloodstream, thus providing high bioavailability of AIs; therefore, required dose may be lower. Additionally, adjustments of AIs dosages may be achieved when using disclosed oral transmucosal compositions.

1 Claim, No Drawings

ORAL TRANSMUCOSAL COMPOSITIONS INCLUDING AROMATASE INHIBITORS FOR LOW TESTOSTERONE LEVELS IN MEN

CROSS-REFERENCE TO RELATED CASES

This application is a continuation of U.S. patent application Ser. No. 15/328,443 entitled ORAL TRANSMUCOSAL COMPOSITIONS INCLUDING AROMATASE INHIBITORS FOR LOW TESTOSTERONE LEVELS IN MEN filed on Jan. 23, 2017 which claims the benefit of a 35 U.S.C. § 371 National Stage Entry of PCTUS2015041560 filed Jul. 22, 2015 which claims priority to Ser. No. 14/337,783 entitled ORAL TRANSMUCOSAL COMPOSITIONS INCLUDING AROMATASE INHIBITORS FOR LOW TESTOSTERONE LEVELS IN MEN, filed on Jul. 22, 2014, the contents of which are hereby incorporated by reference.

BACKGROUND

Field of the Disclosure

The present disclosure relates generally to pharmaceutical compositions, and more particularly, to oral transmucosal compositions including a plurality of aromatase inhibitors for testosterone deficiency or high estradiol in men.

Background Information

Testosterone is the androgenic hormone primarily responsible for normal growth and development of male sex and reproductive organs, including the penis, testicles, scrotum, prostate, and seminal vesicles. It facilitates the development of secondary male sex characteristics such as musculature, bone mass, fat distribution, hair patterns, laryngeal enlargement, and vocal cord thickening, among others. Additionally, normal testosterone levels maintain energy level, healthy mood, fertility, and sexual desire.

The testes produce testosterone and are regulated by a complex chain of signals that begins in the brain. This chain is called the hypothalamic-pituitary-gonadal axis. The hypothalamus secretes gonadotropin-releasing hormone (GnRH) to the pituitary gland in pulses (bursts) which trigger the secretion of luteinizing hormone (LH) from the pituitary gland. Luteinizing hormone stimulates the Leydig cells of the testes to produce testosterone. Normally, the testes produce approximately 4 mg to 7 mg of testosterone per day.

Testosterone production declines naturally with age. Low testosterone, or testosterone deficiency (TD), may result from disease or damage to the hypothalamus, pituitary gland or testicles that inhibits hormone secretion and testosterone production, and is also known as hypogonadism. Depending on age, insufficient testosterone production can lead to abnormalities in muscle and bone development, underdeveloped genitalia and diminished virility.

Testosterone deficiency can be treated by intramuscular injections at intervals of 7 to 21 days, a testosterone patch worn on the body, transdermal testosterone gels, mucoadhesive material applied above the teeth twice a day, oral tablets, long-acting subcutaneous implants, testosterone stick applicators (applied similar to underarm deodorant), injectable pellets, and the like.

Typically, testosterone therapy is administered orally, parenterally, transdermally, or through buccal administration. Additionally, testosterone therapy typically involves very high doses of testosterone.

Oral therapy of testosterone lacks effectiveness because testosterone is metabolized extensively during the first passage of the liver before reaching the systemic blood circulation (i.e., the first-pass effect). Intramuscular injections of testosterone esters are widely used, but local pain, tolerability, and the unphysiologically high levels of testosterone in the body during the first days/weeks after injection are severe drawbacks to this form of treatment. Local pain is attributed to the large volumes of testosterone injected and the required help of health care professionals makes injections inconvenient and expensive. These same drawbacks also apply to implanted pellets.

Transdermal administration (e.g., patches, gels, etc.) has the benefit that the first-pass effect is avoided and the treatment is not painful. Unfortunately, transdermal compositions, excluding patches, currently prescribed for hypogonadal men include from 40 mg to 120 mg (dosed daily) of which only a low percentage is absorbed through the skin. Another drawback is that a large part of the testosterone remains on the skin, with the potential risk of transferring the medication to the skin of another person when direct skin-to-skin contact is made. Additionally, the non-absorbed portion of testosterone is lost to the surrounding environment making these formulations non-environmentally-friendly. Additionally, a common side effect of transdermal compositions is local skin irritation. This is likely due to the very high ethanol content of such formulations.

Oral transmucosal delivery is a particularly advantageous delivery route. One of the advantages of oral transmucosal delivery is that it is a non-invasive drug delivery method. Furthermore, oral transmucosal delivery has better patient compliance, less risk of infection, and lower cost than invasive procedures such as injection and implantation. Oral transmucosal delivery also results in much shorter onset time (i.e., the time from administration to therapeutic effect) than oral delivery does. The active pharmaceutical ingredient (API) absorbed when using oral transmucosal delivery via the oral mucosa will also avoid degradation in the gastrointestinal tract and first pass metabolism in the liver. Oral transmucosal delivery is simple and can be administered by a caregiver or the patient with minimal discomfort.

Oral transmucosal administration involves the patient holding the compositions in the oral cavity while the APIs dissolves in the fluid available, diffuses through the mucosa lining of the mouth, and is absorbed directly into the bloodstream bypassing the gastrointestinal tract as well as hepatic metabolism.

Recently, research studies have demonstrated that aromatase inhibitors (AIs) as APIs may be used for male testosterone therapy. AIs work by binding to the aromatase enzyme that converts testosterone into estrogen. Estradiol serves as a major mediator of sex steroid-gonadotropin feedback; hence, high estradiol levels could contribute to low testosterone production through inhibition of LH. However, high estradiol levels can exist independently of testosterone levels. AIs effectively inhibit or block conversion of testosterone into estrogen which leads to increased LH and follicle-stimulating hormone (FSH) release from the pituitary. Increased LH and FSH results in a subsequent increase in testicular stimulation and serum testosterone levels without the increase in estrogen levels, and thus could limit the likelihood of undesirable effects such as gynecomastia. However, there are no AI products on the market for treatment of either testosterone deficiency or high estradiol in men.

For the aforementioned reasons, there is a need for oral transmucosal dosage forms, including AIs, which can deliver AIs directly into the patient's bloodstream with a high percentage of bioavailability.

SUMMARY

The present disclosure refers to oral transmucosal compositions that may include one or more aromatase inhibitors (AIs) in order to increase testosterone levels in a patient's bloodstream and reduce symptoms of testosterone deficiency. According to some embodiments, the oral transmucosal compositions may include different components, such as active pharmaceutical ingredients (APIs), transmucosal absorption enhancers, suitable vehicles, and suitable additives, among others.

According to one embodiment, APIs may include selective AIs such as Anastrozole (Arimidex), Letrozole (Femara), Exemestane (Aromasin), Vorozole (Rivizor), Formestane (Lentaron), and Fadrozole (Afema). In another embodiment, APIs may include non-selective AIs such as Aminoglutethimide, and Testolactone (Teslac). In yet another embodiment, APIs may include any other selective or non-selective chemical known to people skilled in the art that inhibits the enzyme aromatase and may prevent estrogen from being formed from its metabolic precursors.

In an example, the AI employed in oral transmucosal compositions may be Anastrozole, Exemestane, or Letrozole.

In some embodiments, various additives may be included to facilitate the preparation of suitable dosage forms. For example, additives may include diluents, binders, disintegrants, lubricants, glidants, mucoadhesive polymers, thickening agents, transmucosal absorption enhancers, polymer plasticizers, pH adjusters, preservatives, sweeteners, flavors, colors, effervescent agents, stabilizing agents, antioxidants, and surfactants, among others. Additives are known to those skilled in the art.

In some embodiments, transmucosal absorption enhancers provide more efficient API skin and mucosal tissue penetration. In these embodiments, the transmucosal absorption enhancers allow lower API dosage requirements.

In some embodiments, oral transmucosal compositions allow the delivery of AIs directly into the patient's bloodstream bypassing the gastrointestinal tract and the hepatic metabolism. In these embodiments, bypassing the gastrointestinal tract and the hepatic metabolism results in a higher percentage of bioavailability of AIs to the patient. Further to these embodiments, adjustments of AIs dosages may be achieved when using the disclosed oral transmucosal compositions.

In some embodiments, oral transmucosal compositions may provide dosage regimens of AIs that are tailored for individual patients. In an example, depending on the baseline serum concentrations of testosterone and estradiol in a patient, a medical doctor may prescribe an oral transmucosal composition with a dosage regimen to more closely mimic the circadian rhythm and physiological pulsatile secretion of testosterone thereby keeping the testosterone and estradiol levels within suitable ranges.

Examples of oral transmucosal compositions that may be administered include dosage ranges of: about 0.05 mg/day to about 1.0 mg/day of Anastrozole, preferably about 0.1 mg/day to about 0.5 mg/day; about 10 mg/day to about 50 mg/day of Exemestane, preferably about 25 mg/day to about 50 mg/day; or about 0.025 mg/day to about 5.0 mg/day of Letrozole, preferably about 0.25 mg/day to about 2.5 mg/day.

In some embodiments, oral transmucosal compositions may include liquid dosage forms such as sublingual solutions, emulsions, suspensions, and liquid sprays, among others. In other embodiments, oral transmucosal compositions may include solid dosage forms such as sublingual tablets, and buccal troches, among others. In yet other embodiments, oral transmucosal dosage forms may include chewing gums.

In some embodiments, oral transmucosal dosage forms include mucoadhesive polymers as part of the compositions. Examples of dosage forms include mucoadhesive thin strips, thin films, tablets, patches, and tapes, among others. In other embodiments, dosage forms include: mucoadhesive liquids such as gel-forming liquid; semisolids such as gels, gel-forming ointments, and gel-forming pastes; gel-forming powders, or any other dosage forms that exhibit mucoadhesive properties and provide oral transmucosal delivery of AIs.

Absorption sites, within the oral cavity, for oral transmucosal dosage forms may be sublingual, buccal, gingival, palatal, or the like.

In some embodiments, providing low dose formulations in any of the above identified methodologies will result in acceptable testosterone levels in the patient. This contrasts with current popular topical treatment options, which use very high dosages of testosterone to get a few milligrams of testosterone absorbed into the bloodstream.

In some embodiments, dosage forms are designed for immediate release and transmucosal absorption of AIs. In other embodiments, AIs may be released and absorbed over a prolonged period of time for systemic effects.

Numerous other aspects, features, and benefits of the present disclosure may be made apparent from the following detailed description.

DETAILED DESCRIPTION

The present disclosure is here described in detail. Other embodiments may be used and/or other changes may be made without departing from the spirit or scope of the present disclosure. The illustrative embodiments described in the detailed description are not meant to be limiting of the subject matter presented here.

Definitions

As used here, the following terms may have the following definitions:

"Active Pharmaceutical Ingredient (API)" refers to a chemical compound that induces a desired effect, and includes agents that are therapeutically effective, prophylactically effective, or cosmeceutically effective.

"Adsorption Enhancer" or, equivalently, "Penetration Enhancer" refers to a substance used to modify, generally to increase, the rate of permeation through skin or other body tissue of one or more substances (e.g., APIs) in a formulation.

"Aromatase Inhibitor (AI)" refers to a chemical compound that blocks or inhibits the activity of aromatase which is an enzyme that converts androgens to estrogens. As such, an aromatase inhibitor acts to reduce estrogen levels in the body.

"Treating" and "Treatment" refers to reduction in severity and/or frequency of symptoms, elimination of symptoms and/or underlying cause, prevention of the occurrence of symptoms and/or their underlying cause, and improvement or remediation of damage.

"Vehicle" refers to a substance of no therapeutic value that is used to convey at least one API for administration.

DESCRIPTION OF THE DISCLOSURE

Embodiments of the present disclosure are directed towards oral transmucosal delivery of active pharmaceutical ingredient (APIs). Oral transmucosal compositions that include one or more aromatase inhibitors (AIs) as APIs are described. The present disclosure including AIs is proposed to increase testosterone levels in a patient's bloodstream and reduce symptoms of testosterone deficiency.

Estradiol serves as a major mediator of sex steroid-gonadotropin feedback; hence, high estradiol levels could contribute to low testosterone production through inhibition of luteinizing hormone (LH). Aromatase inhibitors block the formation of estradiol and can limit the inhibition of LH. High estradiol levels can exist independently of testosterone levels and AIs may limit the likelihood of undesirable effects from estradiol such as gynecomastia.

Formulation

Oral transmucosal compositions may include one or more AIs as APIs, transmucosal absorption enhancers, vehicles, and additives, among other suitable ingredients.

According to one embodiment, APIs may include selective AIs such as Anastrozole (Arimidex), Letrozole (Femara), Exemestane (Aromasin), Vorozole (Rivizor), Formestane (Lentaron), and Fadrozole (Afema). In another embodiment, APIs may include non-selective AIs such as Aminoglutethimide, and Testolactone (Teslac). In yet another embodiment, APIs may include any other selective or non-selective chemical known to people skilled in the art that inhibits the enzyme aromatase and may prevent estrogen from being formed from its metabolic precursors.

The list of AIs above is not exhaustive; other compounds described in the art that meet the set requirements may also be considered.

In an example, the AI employed in oral transmucosal compositions may be Anastrozole, Exemestane, or Letrozole.

In some embodiments, various additives may be included to facilitate the preparation of suitable dosage forms. For example, additives may include diluents, binders, disintegrants, lubricants, glidants, mucoadhesive polymers, thickening agents, transmucosal absorption enhancers, polymer plasticizers, pH adjusters, preservatives, sweeteners, flavors, colors, effervescent agents, stabilizing agents, antioxidants, and surfactants, among others. Additives are known to those skilled in the art.

In some embodiments, transmucosal absorption enhancers provide more efficient API skin and mucosal tissue penetration. In these embodiments, the transmucosal absorption enhancers allow lower API dosage requirements.

In some embodiments, diluents for solid dosage forms may include calcium carbonate, dibasic calcium phosphate, tribasic calcium phosphate, calcium sulfate, kaolin, microcrystalline cellulose, and other cellulose derivates, sodium chloride, starch and starch derivates, sucrose, dextrose, lactose, and sorbitol, among others.

Binders for solid dosage forms may include starch and starch derivatives, gelatin, sucrose, glucose, dextrose, molasses, lactose, natural and synthetic gums, acacia, sodium alginate, extract of Irish Moss, panwar gum, ghatti gum, mucilage of isapol husks, carboxymethylcellulose, methylcellulose, cellulose derivatives, Veegum, polyvinylpyrolidone, and polyethylene glycols, among others.

Disintegrants for solid dosage forms may include veegum, agar, bentonite, alginic acid and alginic acid derivatives, guar gum, starch, sodium starch glycolate, other starch derivatives, clays, cellulose, and cellulose derivatives, among others.

Lubricants for solid dosage forms may include stearic acid, stearic acid derivatives, stearic acid salts such as magnesium stearate and calcium stearate, talc, hydrogenated vegetables oils, polyethylene glycols, surfactants, and waxes, among others.

Additionally, solid dosage forms of oral transmucosal compositions may include: a glidant, such as colloidal silicon dioxide and talc, among others; a sweetening agent, such as sucrose or saccharin, among others; natural or artificial flavors, such as peppermint, methyl salicylate, or orange flavor, among others.

The pH adjusting agents may include sodium bicarbonate, magnesium hydroxide, calcium carbonate, dibasic calcium phosphate, tribasic calcium phosphate, sodium bicarbonate, magnesium hydroxide, potassium hydroxide, citric acid, lactic acid, hydrochloric acid, sulfuric acid, phosphoric acid, sodium phosphate monobasic, and sodium phosphate dibasic, among others.

Surfactants may include: polysorbates such as polysorbate 20, 40, 60, and 80, among others; sorbitan esters such as sorbitan monolaurate, and sorbitan monopalmitate, sorbitan monooleate, among others; and sodium lauryl sulfate, among others.

Effervescent agents are usually a combination of one or more acids with one or more bases. Acids may be selected from citric acid, tartaric acid, and the like. Bases may be sodium bicarbonate or other suitable agents that may react with acids, and produce gas.

In some embodiments, a stabilizing agent may be used to stabilize the API for a specific dosage form. In these embodiments, the stabilizing agent used will depend on the API used as well as the other additive ingredients. Any suitable chemical substance may be used as a stabilizing agent. Stabilizing agents are known in the art and will not be discussed further.

Mucoadhesive polymers may include: gums such as acacia, agarose, alginic acid, sodium alginate and other alginic acid derivatives, carrageenan, gelatin, gellan, guar gum, hakea gum, karaya gum, and locust bean gum, among others; chitosan and chitosan derivatives; hyaluronic acid, pectin, and other polysaccharides; gelatin, polyisoprene, polyisobutylene, polyetherurethane, polyvinylalcohol, polyvinylpyrrolidone, polycarbophil, polyethylene oxide polymers, and pullulan, among others. Mucoadhesive polymers may also include cellulose derivatives such as ethyl cellulose, cellulose acetate, hydroxyethyl cellulose, hydroxypropylcellulose, hydroxypropylmethylcellulose, methylcellulose, methylhydroxyethylcellulose, and sodium carboxymethyl cellulose, among others; poly(acrylic acid)-based polymers such as polyacrylates, poly (methylvinylether-co-methacrylic acid), poly(acrylic acid-co-ethylhexylacrylate), poly(acrylic acid-co-acrylamide), poly(acrylic acid-co-butylacrylate), poly(acrylic acid-co-methyl methacrylate), poly (2-hydroxyethyl methacrylate), polymethacrylates, poly(alkylcyanoacrylate) and other cyanoacrylates, poly (isohexycyanoacrylate), poly (isobutylcyanoacrylate), and hydroxyethyl methacrylate, and any other polymer known to a person skilled in the art that exhibits mucoadhesive characters.

Plasticizers for mucoadhesive polymeric dosage forms may include pullulan, hydroxypropyl methylcellulose, propylene glycol, glycerol, sorbitol, mannitol, polyethylene glycols (PEG 200, 400, 600, 1000, 1500, 2000), tartaric acid, malic acid, lactic acid, citric acid, and yonkenafil, and any other chemical known to a person skilled in the art that can increase the plasticity of any mucoadhesive polymer.

Oral transmucosal absorption enhancers may include: enzyme inhibitors such as aprotinin and puromycin, among others; chitosan and chitosan derivatives such as chitosan glutamate, trimethyl chitosan, chitosan-4-thioglycolic acid, 5-methyl-pyrrolidine chitosan, and chitosan-4-thio-butyl-amidine, among others; alpha, beta, and gama cyclodextrins such as dimethyl cyclodextrin, sulfobutyl cyclodextrin, 2-hydroxypropyl-beta-cycldextrin, poly-beta-cyclodextrin, and methylated beta-cyclodextrin, among others; bile salts such as sodium deoxycholate, sodium glycocholate, sodium glycodeoxycholate, sodium glycodihydrofusidate, sodium taurocholate, sodium taurodeoxycholate, sodium taurogly-cocholate, sodium taurodihydrofusidate, and sodium urso-cholate, among others; chelating agents such as sodium EDTA, citric acid, sodium citrate, sodium salicylate, methylsalicylate, methoxysalicylate, and polyacrylates, among others; alcohols such as ethanol and isopropanol, among others; fatty acids and derivatives such as oleic acid, methyloleate, capric acid, neodecanoic acid, elaidic acid, lauric acid, palmitoylearnitine, cod liver oil extract, mono glycerides and diglycerides of oleic acid andcapric acid, lauric acid, sodium laurate, linoleic acid, sodium fusidate, sodium caprate, lyceryl monolaurate, glyceryl monooleate, glyceryl monostearate, sucrose fatty acid esters, and diethylene glycol monoethyl ether, among others; lecithins and phospholipids such as phodphatidylcholine, lysophosphatidyl choline, and didecanoylphophatidylcholine, among others; sulfoxides such as dimethylsulfoxide and decylmethyl sulfoxide, among others; polyols such as glycerin, propylene glycol, propanediol, and polyethylene glycols of various molecular weights, among others; urea and derivatives such as unsaturated cyclic urea, among others; surfactants such as sodium dodecyl sulfate, sodium lauryl sulfate, dioctyl sodium sulfosuccinate, nonylphenoxypolyoxyethylene, polyoxyethylene alkyl ethers, polyoxyethylene-9-lauryl ether, polyoxyethylene 23 lauryl ether, polyoxyethylene-20-cetyl ether, polyethyleneglycol dodecyl ether, polyethylene glycol-8 laurate, glyceryl monolaurate, polyoxyethylene stearates, polysorbates, sorbitan fatty acid esters, polyoxyethylene castor oil derivatives, benzalkonium chloride, cetylpyridinium chloride, and cetyltrimethylammonium bromide, among others. Other oral transmucosal absorption enhancers may include alkylglycosides, azone, hyaluronic acid, sodium Hyaluronate, glycine chenodeoxycholate, lauroyl macroglycerides, isopropyl myristate, isopropyl palmitate, glutathione, witepsol, menthol, capsaicin, taurine, tocopheryl acetate, lauroyl macroglycerides, lionoleoyl polyoxyl-6 glycerides; diethylene glycol monoethyl ether, dextran sulfate, various saponins, poly-1-arginine, and 1-lysine, and any other chemical known to a person skilled in the art that exhibits penetration enhancing effect on transmucosal absorption.

Bases for chewing gum may include cellulosic polymer, and acrylic polymer, among others.

In some embodiments, oral transmucosal compositions may include pharmaceutical solvents to produce sprays, solutions, emulsions, suspensions, gels, gel-forming liquids, ointments and pastes, among others.

In some embodiments, pharmaceutical solvents for liquid dosage forms of oral transmucosal compositions may include water, liquid polyethylene glycols of various molecular weights, ethyl oleate, medium chain triglycerides, isopropyl myristate, isopropyl palmitate, isopropyl stearate, other pharmaceutically acceptable esters of C8-C22 fatty acids and C2-C6 alcohols, mineral oil, and vegetable oils, among others.

C8-C22 fatty acids may include fatty acids having from 8 to 22 carbon atoms, such as myristic acid, palmitic acid, stearic acid, arachidic acid, or oleic acid, among others.

C2-C6 alcohols may include alcohols having from 2 to 6 carbon atoms, in particular the C2-C5 alcohols as well as the homologues with 6 carbon atoms including diols and triols such as ethanol, propylene glycol, and glycerol, among others.

Examples of vegetable oils may include almond oil, peanut oil, sesame oil, sunflower oil, safflower oil, canola oil, corn oil, and olive oil, among others.

In some embodiments, oral transmucosal ointments and pastes may include petrolatum, PCCA plasticized base, paraffin wax, various synthetic wax, lanolin, beeswax, carnauba wax, candelila wax, silicones, isopropylesters, polyols, cellulose ethers, among other suitable bases. In addition, ointment bases may also include suitable pharmaceutical solvents, such as water, liquid polyethylene glycols of various molecular weights, ethyl oleate, medium chain triglycerides, isopropyl myristate, isopropyl palmitate, isopropyl stearate, and other pharmaceutically acceptable esters of C8-C22 fatty acids and C2-C6 alcohols, mineral oil, and vegetable oils, among others.

Administration

In some embodiments, oral transmucosal compositions allow the delivery of AIs directly into the patient's bloodstream bypassing the gastrointestinal tract and the hepatic metabolism. In these embodiments, bypassing the gastrointestinal tract and the hepatic metabolism results in a higher percentage of bioavailability of AIs to the patient. Further to these embodiments, adjustments of AIs dosages may be achieved when using the disclosed oral transmucosal compositions.

In some embodiments, oral transmucosal compositions may be administered in the oral cavity at the sublingual, palatal, buccal, gingival, or the like. Oral transmucosal compositions may be self-administered by the patient or administered by a medical practitioner, such as a physician or nurse.

In some embodiments, oral transmucosal compositions may include liquid dosage forms such as sublingual solutions, emulsions, suspensions, and liquid sprays, among others. In other embodiments, oral transmucosal compositions may include solid dosage forms such as sublingual tablets, and buccal troches, among others. In yet other embodiments, oral transmucosal dosage forms may include chewing gums.

In some embodiments, oral transmucosal dosage forms include mucoadhesive polymers as part of the compositions. Examples of dosage forms include mucoadhesive thin strips, thin films, tablets, patches, and tapes, among others. In other embodiments, dosage forms include: mucoadhesive liquids such as gel-forming liquid; semisolids such as gels, gel-forming ointments, and gel-forming pastes; gel-forming powders, or any other dosage forms that exhibit mucoadhesive properties and provide oral transmucosal delivery of AIs.

Absorption sites, within the oral cavity, for oral transmucosal dosage forms may be sublingual, buccal, gingival, palatal, or the like.

In some embodiments, dosage forms are designed for immediate release and transmucosal absorption of AIs. In other embodiments, AIs may be released and absorbed over a prolonged period of time for systemic effects.

In some embodiments, oral transmucosal compositions may be administered in a single administration whereby a certain amount of AI may be administered at once. In an example, one puff of a spray solution may be administered representing the full desired dose. In other embodiments, oral transmucosal compositions may be administered by multiple administrations in one or more sub-doses over a specified period of time. In an example, one, two or more puffs of a smaller dose may be administered preferably shortly after one another.

In some embodiments, oral transmucosal compositions may provide dosage regimens of AIs that are tailored for individual patients. In an example, depending on the baseline serum concentrations of testosterone and estradiol in a patient, a medical doctor may prescribe an oral transmucosal composition with a dosage regimen to more closely mimic the circadian rhythm and physiological pulsatile secretion of testosterone thereby keeping the testosterone and estradiol levels within suitable ranges.

In some embodiments, providing low dose formulations in any of the above identified methodologies will result in acceptable testosterone levels in the patient. This contrasts with current popular topical treatment options, which use very high dosages of testosterone to get a few milligrams of testosterone absorbed into the bloodstream.

In various embodiments, the dosages (e.g., daily) required depend on the type of AI included in the disclosed oral transmucosal compositions. In other words, some AIs are more potent than others, and hence, the dosing can vary among the various AIs used.

Examples of oral transmucosal compositions that may be administered include dosage ranges of: about 0.05 mg/day to about 1.0 mg/day of Anastrozole, preferably about 0.1 mg/day to about 0.5 mg/day; about 10 mg/day to about 50 mg/day of Exemestane, preferably about 25 mg/day to about 50 mg/day; or about 0.025 mg/day to about 5.0 mg/day of Letrozole, preferably about 0.25 mg/day to about 2.5 mg/day.

In some embodiments, providing low dose oral transmucosal compositions allows controlling the increase of testosterone levels in relation to the administered dosages of AIs.

The following examples are intended to illustrate the scope of the disclosure and are not intended to be limiting. It is to be understood that other procedures known to those skilled in the art may alternatively be used.

EXAMPLES

The following are exemplary of dosage forms of the oral transmucosal compositions.

Example #1 illustrates formula for one Anastrozole sublingual tablet:

| Ingredient | Composition |
| --- | --- |
| Anastrozole | 0.1-0.5 mg |
| Penetration enhancer(s) | Appropriate concentration |
| Lactose/sucrose (80:20) | q.s. 100% |

Example #2 illustrates formula for one dose of Anastrozole sublingual drops:

| Ingredient | Composition |
| --- | --- |
| Anastrozole | 0.1-0.5 mg |
| Co-solvent(s) | 10-50% |
| Penetration enhancer(s) | Appropriate concentration |
| Flavors | As needed |
| Sweeteners | As needed |
| Base Solvent (Glycerin) | q.s. 100% |

Example #3 illustrates formula for one dose of Letrozole oral adhesive paste:

| Ingredient | Composition |
| --- | --- |
| Letrozole | 0.25-2.5 mg |
| Gelatin | 1-5% |
| Pectin | 1-5% |
| Sodium Carboxymethylcelluose | 1-10% |
| Xanthan gum | 0.1-5% |
| PEG-90M | 1-10% |
| Penetration enhancer(s) | Appropriate concentration |
| PCCA Plasticized Base | q.s. 100% |

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A method of oral transmucosal delivery of aromatase inhibitors into a patient's bloodstream consisting of:
   administering to the patient a composition consisting of:
   (a) about 0.25 to about 2.5 mg letrozole;
   (b) about 1-5% gelatin;
   (c) about 1-5% pectin;
   (d) about 1-10% sodium carboxymethylcellulose;
   (e) about 0.1-5% xanthan gum;
   (f) 1-10% polyethyleneglycol;
   (g) a penetration enhancer; and
   (h) a plasticized base.

* * * * *